United States Patent
von Bebenburg et al.

[11] 3,972,873
[45] *Aug. 3, 1976

[54] CERTAIN PYRIDO[3,2-e]1,4-DIAZEPINONES AND DERIVATIVES

[75] Inventors: Walter von Bebenburg, Buchschlag; Heribert Offermanns, Grossauheim, both of Germany

[73] Assignee: Deutsche Gold- und Silber-Scheideanstalt vormals Roessler, Germany

[ * ] Notice: The portion of the term of this patent subsequent to Aug. 19, 1992, has been disclaimed.

[22] Filed: May 9, 1975

[21] Appl. No.: 576,112

Related U.S. Application Data

[63] Continuation-in-part of Ser. No. 468,088, May 8, 1974, Pat. No. 3,900,466.

[30] Foreign Application Priority Data

May 25, 1973 Austria .............................. 4628/73

[52] U.S. Cl. ..................... 260/239.3 B; 260/294.8C; 260/294.9; 260/295 K; 424/263
[51] Int. Cl.² ....................................... C07D 471/04
[58] Field of Search .................. 260/295 K, 294.8 C, 260/294.9, 239.3

[56] References Cited
UNITED STATES PATENTS
3,910,887  10/1975  von Bebenburg ............ 260/239.3 B OTHER PUBLICATIONS
Chem. Substance Index (j-Z) p. 3189CS of Chem Abstracts vol. 79 Dec. 31, 1973

*Primary Examiner*—Alan L. Rotman
*Attorney, Agent, or Firm*—Cushman, Darby & Cushman

[57] ABSTRACT

There are prepared compounds of the formula:

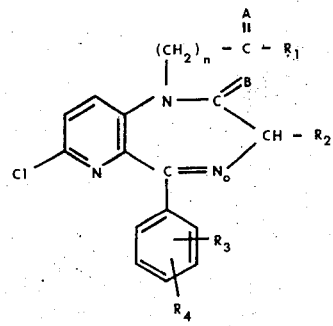

wherein:
  n is an integer from 1 to 4;
  $R_1$ is alkyl of 1 to 6 carbon atoms, a hydroxy group, an amino group, an alkoxy group having 1 to 6 carbon atoms, a phenyl group or a phenyl group substituted with alkyl of 1 to 6 carbon atoms, an alkoxy group of 1 to 6 carbon atoms, trifluoromethyl, fluorine or chlorine;
  A is oxygen, sulfur, the imino group, or an alkylimino group having 1 to 6 carbon atoms, or when $R_1$ is phenyl or substituted phenyl A also is two alkoxy groups having 1 to 6 carbon atoms or alkylenedioxy with 2 to 4 carbon atoms or —C($R_1$)=A is the cyano group;
  B is oxygen, sulfur, an imino group or an alkylimino group having 1 to 6 carbon atoms;
  $R_2$ is hydrogen, a hydroxy group, an alkyl group with 1 to 6 carbon atoms, an alkoxy group with 1 to 6 carbon atoms, or the group —O(CH$_2$)$_n$—C(=A)—$R_1$;
  $N_o$ is nitrogen or an N-oxide group; and
  $R_3$ and $R_4$ are the same or different and are hydrogen, chlorine, fluorine, the trifluoromethyl group, alkyl groups of 1 to 6 carbon atoms or alkoxy groups with 1 to 6 carbon atoms, the tautomeric forms thereof and pharmaceutically acceptable salts thereof. The compounds have psychosedative, anxiolytic, spasmolytic and antipsychotic activity.

25 Claims, No Drawings

CERTAIN PYRIDO[3,2-e]1,4-DIAZEPINONES AND DERIVATIVES

This application is a continuation-in-part of application Ser. No. 468,088 filed May 8, 1974, now U.S. Pat. No. 3,900,466 dated Aug. 19, 1975.

The present invention is concerned with new 3H-pyrido [3,2-e]-1,4-diazepines of the formula:

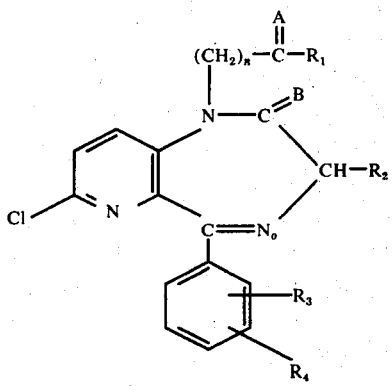

wherein:
  $n$ is an integer from 1 to 4;
  $R_1$ is alkyl of 1 to 6 carbon atoms, a hydroxy group, an amino group, an alkoxy group having 1 to 6 carbon atoms, a phenyl group or a phenyl group substituted with alkyl of 1 to 6 carbon atoms, an alkoxy group of 1 to 6 carbon atoms, trifluoromethyl, fluorine or chlorine;
  A is oxygen, sulfur, the imino group, or an alkylimino group having 1 to 6 carbon atoms, or when $R_1$ is phenyl or substituted phenyl, A also is two alkoxy groups having 1 to 6 carbon atoms or alkylenedioxy with 2 to 4 carbon atoms or —C($R_1$)=A is the cyano group;
  B is oxygen, sulfur, an imino group or an alkylimino group having 1 to 6 carbon atoms;
  $R_2$ is hydrogen, a hydroxy group, an alkyl group with 1 to 6 carbon atoms, an alkoxy group with 1 to 6 carbon atoms, or the group —O(CH$_2$)$_n$ — C(=A-)—R$_1$;
  $N_o$ is nitrogen or an N-oxide group; and
  $R_3$ and $R_4$ are the same or different and are hydrogen, chlorine, fluorine, the trifluoromethyl group, alkyl groups of 1 to 6 carbon atoms or alkoxy group with 1 to 6 carbon atoms, the tautomeric forms thereof and pharmaceutically acceptable salts thereof.

Preferably the alkyl groups, alkoxy groups and alkylimino groups preferably have 1 to 4 carbon atoms.

In the event $R_1$ is a substituted phenyl group it can be mono or di substituted and the substituents can be the same or different. In the event that A is an alkylenedioxy group preferably it is the ethylenedioxy group, i.e., A with the attached carbon atom forms the dioxolane ring.

Examples of alkyl and alkoxy groups which can be present include methyl, ethyl, propyl, isopropyl, butyl, tert.butyl, sec. butyl, amyl, hexyl, isobutyl, methoxy, ethoxy, isopropoxy, butoxy, isobutoxy, tert. butoxy, amyloxy, hexoxy, propoxy. Examples of alkylimino groups are methylimino, ethylimino, propylimino, butylimino, hexylimino, sec. butylimino.

The group —C(=B)—CHR$_2$— in a given case can also be present in the isomeric or tautomeric form —C(BR$_z$)=CH—.

In addition to the compounds mentioned in the working examples the other compounds within the present invention include:

1-acetylmethyl-5-phenyl-7-chloro-3H- pyrido[3,2-e]-diazepinone-(2);
1-acetylethyl-5-(o-fluorophenyl)-7-chloro-3H-pyrido[3,2-e]-1,4-diazepinone-(2);
1-propionylmethyl-5-phenyl-7-chloro-3H-pyrido[3,2e]-1,4-diazepinone-(2);
1-butyrylmethyl-5-phenyl-7-chloro-3H-pyrido[3,2-e]-1,4-diazepinone-(2);
1-hexanoylmethyl-5-(o-chlorophenyl)-7-chloro-3H-pyrido[3,2-e]-1,4-diazepinone-(2);
1-(2-cyanoethyl)-3hydroxy-5-phenyl-7-chloro-3H-pyrido[3,2-e]-diazepinone-(2);
1-(3-cyanopropyl-(1))-3-methyl-5-phenyl-7-chloro-3H-pyrido[3,2-e]-1,4-diazepinone-(2);
1-(3-cyanopropyl-(1))-5-phenyl-7-chloro-3H-pyrido[3,2-e]-1,4-diazepinone-(2)-4-oxide.

The compounds of the invention have valuable pharmacodynamic properties. For example, they have psychosedative and anxiolytic (tranquilizing), spasmolytic and antipsychotic properties.

The compounds of formula I can be prepared by methods which are known in themselves such as:

a. reacting a compound of the formula:

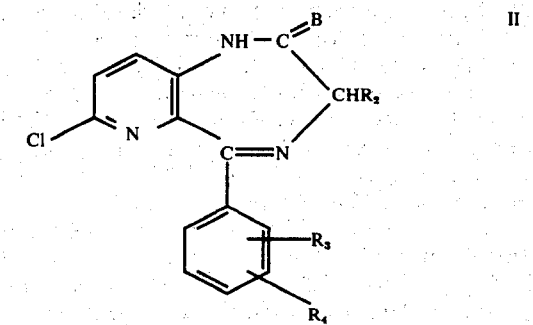

with a compound of the formula:

wherein A, $R_1$ and $n$ are as defined above and X is a chlorine, bromine or iodine atom or an azido group, or X and $R_1$ together are an oxygen atom (—O—) in a lactone ring when $n$ is 2, 3 or 4;

b. condensing a compound of the formula:

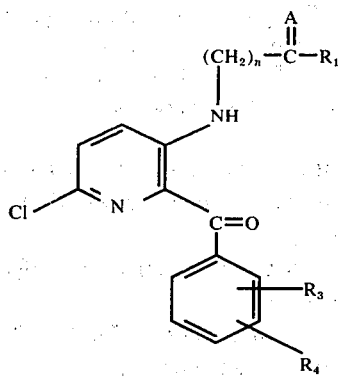

with a compound of the formula:

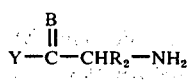

wherein $R_2$ and B are as defined above and Y is a hydroxy group, a halogen atom, an alkoxy group, a mercapto group, an alkyl mercapto group, an amino group or an alkylamino group, in a given case with addition of an acid binding agent, or c. in a compound of formula I one or more of the symbols $R_1$, $R_2$, A and $N_o$ can be changed to give a compound of corresponding meaning.

Process (a) is carried out, in a given case with the addition of customary acid binding agents such as alkali carbonates, e.g., sodium carbonate or potassium carbonate, pyridine or other customary tertiary amines, e.g., triethyl amine, at temperatures between 0° and 150°C. in inert solvents such as dioxane, dimethyl formamide, dimethyl sulfoxide, aromatic hydrocarbons such as benzene and toluene or acetone. It is also possible to proceed by first producing an alkali compound of the compound of formula II which is to be reacted, by reacting the compound of formula II in an inert solvent such as dioxane, dimethyl formamide, benzene or toluene with an alkali metal, alkali hydride or alkali amide (especially sodium, sodium hydride or sodamide) at temperatures between 0° and 150°C. and then adding the compound of formula III.

Process (b) takes place in customary solvents or suspension media at temperatures between 0° and 200°C., preferably 20° to 150°C. Especially there can be employed polar solvents, for example, alcohols, e.g., methyl alcohol, ethyl alcohol, propyl alcohol, isopropyl alcohol and butyl alcohol, dioxane, tetrahydrofurane, dimethyl sulfoxide, dimethyl formamide or imidazole, as well as media such as pyridine or quinoline. In case Y is a halogen atom it can be advantageous (but otherwise there should not be added) to add basic materials, e.g., sodium hydroxide, which facilitate an acid splitting. In case Y is a hydroxy group it is suitable and sometimes necessary to add customary water splitting off (dehydrating) agents such as dicyclohexylcarbodiimide or 1-ethoxy-2-carbethoxy-1,2-dihydroquinoline. In case Y is an alkylmercapto group, alkoxy group or alkylamino group these groups are preferably of lower molecular weight and for example consist of 1 to 6 carbon atoms, e.g., methyl mercapto, hexyl mercapto, methoxy, ethoxy, methylamino and hexyl amino.

Frequently process (b) can also be carried out in such manner that the amino group in the 3-position of formula IV and/or the amino group of formula V ($Y=NH_2$) carries a protective group known in itself. Frequently such protective groups are already required for the production of the starting compounds. In many cases the splitting off of such a protective group takes place simultaneously with the cyclization.

These protective groups are easily split off. There are employed either easily solvolytically splittable acyl groups or groups splittable by hydrogenation, as for example, the benzyl radical. The solvolytically splittable protective groups are split off for example, by saponification with dilute acids or by means of basic substances (potash, soda, aqueous alkali solutions, alcoholic alkali solutions, $NH_3$) at room temperature or with a short boiling. Hydrogenizably splittable groups such as the benzyl group or the carbobenzoxy radical are suitably split off by catalytic hydrogenation in the presence of customary hydrogenation catalysts, especially palladium catalysts, in a solvent or suspension agent, in a given case under elevated pressure. As solvents or suspension agent there can be used water, lower aliphatic alcohols such as methyl alcohol, ethyl alcohol, isopropyl alcohol, butyl alcohol, cyclic ethers such as dioxane or tetrahydrofurane, aliphatic ethers, e.g., diethyl ether, dimethyl formamide, etc. as well as mixtures of these materials.

As protective groups for the amino group there can be used for example, the benzyl group, α-phenylethyl group, benzyl groups substituted in the benzene nucleus as for example, the p-bromo or p-nitrobenzyl group, the carbobenzoxy group, the carbobenzthio group, the trifluroacetyl, the phthalyl radical, the trityl radical, the p-toluenesulfonyl radical and similar groups as well as simple acyl groups such as the acetyl group, formyl group, tert. butylcarboxy group, etc. There can be employed especially the protective groups used in the synthesis of peptides and the splitting processes customarily employed in that process. Among others for this purpose reference is made to Jesse P. Greenstein and Milton Winitz "Chemistry of Amino Acids," John Wiley and Sons, Inc., New York (1961), Vol. 2, pages 883 et seq. Also there can be used carbalkoxy groups (for example of lower molecular weight such as carbmethoxy, carbethoxy and carbpropoxy).

Process (b) can also be carried out under some circumstances so that before the true cyclization there is previously isolated the intermediate product of the formula:

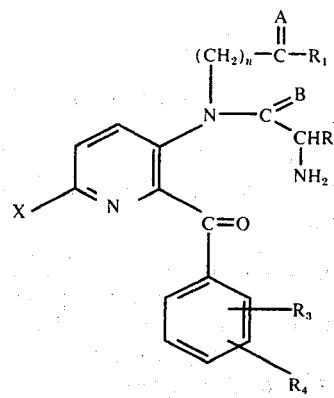

This product can then be cyclized in purified form or as it accumulates. For this purpose there are used temperatures between −70° and +150°C., preferably 0° to 150°C. As solvents or suspending media besides those given above there can be used glacial acetic acid, acetic anhydride, and polyphosphoric acid, using acid condensation agents such as sulfuric acid, hydrochloric acid, hydrobromic acid or toluene sulfonic acid.

Generally it has been found best, however, to carry out the cyclization in an aromatic hydrocarbon, e.g., benzene or toluene, with addition of a tertiary amine, e.g., triethyl amine or pyridine.

According to process (c) pyrido [3,2-e]-diazepines of formula I can be reacted further or substituted in a suitable manner. For example, compounds of formula I wherein $R_1$ is an OH group can be esterified in a suitable manner. For this purpose there can be used for example lower aliphatic alcohols, e.g., of 1 to 6 carbon atoms such as methyl alcohol, ethyl alcohol, isopropyl alcohol, propyl alcohol, butyl alcohol, sec. butyl alcohol, t-butyl alcohol, amyl alcohol, or hexyl alcohol, in the presence of acid catalysts, e.g., hydrochloric acid, sulfuric acid or p-toluene sulfonic acid or there can be reacted diazoalkanes having 1 to 6 carbon atoms, e.g., diazomethane and diazohexane, in the conventional manner in ethereal of dioxane solution at temperatures between 0 and 50°C.

The groups A and B in compounds of formula I can be changed by various procedures. Thus, in case A and B are oxygen, these atoms can be replaced by a sulfur atom by means of phosphorus pentasulfide. This reaction takes place in inert solvents such as benzene, toluene, dioxane, pyridine, of chlorohydrocarbons, e.g., chloroform, at temperatures between 0 and 150°C. Compounds in which A and/or B is oxygen or sulfur can in turn be reacted in polar media (such as those mentioned above, for example) with ammonia alkylamines with 1 to 6 carbon atoms, e.g., methyl amine, ethyl amine, propyl amine, isopropyl amine, butyl amine, amyl amine or hexyl amine to form compounds in which A and/or B are imino or alkylimino groups. The reactions are carried out for example in polar solvents such as methanol, ethanol or excess amine at temperatures between 0° and 150° C.

In case A is two alkoxy groups or an alkylenedioxy group (in which $R_1$ is phenyl or in a given case substituted phenyl) there can be obtained therefrom the ketone where A is O in a manner known in itself using acid conditions. This reaction is carried out for example in polar solvents or suspension media which contain some water, as well as in aqueous methanol, ethanol, dioxane or tetrahydrofurane with the addition of some aqueous hydrochloric acid, sulfuric acid, p-toluene sulfonic acid, etc., or it can also be carried out in aqueous media. The temperature is between 0° and 100°C., preferably at 0° to 20°C.

Conversely, A can be acetalized (for example if A is an oxygen atom). The acetalization is carried out with addition of the alcoholic components, e.g., methyl alcohol, ethyl alcohol, butyl alcohol or hexyl alcohol, in a given case the alcohol being used in excess, in solvents such as dioxane, toluene benzene or also only in the pure alcoholic component with the addition of water free hydrochloric acid, sulfuric acid or p-toluene sulfonic acid, in a given case with azeotropic distillation off of the water formed in the reaction. The temperatures employed are between 0° and 160°C., preferably 50° to 100°C.

Compounds of formula I in which $R_2$ is an alkyl group, an alkoxy group or the group $-O(CH_2)_n - C(=A) - R_1$ can be produced from compounds of formula I in which $R_2$ is H or OH by alkylation. For example, the alkylation takes place by reaction with esters of the formula HalR'', $SO_2(OR'')$ or $ArSO_2OR''$, wherein Hal is a halogen atom, especially Cl, Br or I, Ar is an aromatic radical (especially a phenyl or naphthyl radical, in a given case substituted by one or more lower alkyl groups) and R'' is an alkyl group with 1 to 6 carbon atoms or the group $-(CH_2)_n - C(=A) - R_1$. Examples are p-toluenesulfonic acid alkyl esters, e.g., methyl-p-toluenesulfonate, ethyl-p-toluenesulfonate, lower dialkyl sulfates, e.g., dimethyl sulfate and diethyl sulfate and the like. The alkylation reaction takes place, in a given case, with addition of customary acid binding agents such as alkali carbonate, e.g., sodium carbonate and potassium carbonate, pyridine or other customary tertiary amines at temperatures between 0° and 150° C. in inert solvents such as alcohols, e.g., methyl alcohol, ethyl alcohol or propyl alcohol, dioxane, dimethyl formamide, dimethyl sulfoxide, aromatic hydrocarbons such as benzene or toluene or acetone as well as mixtures of such solvents.

For the alkylation with alkyl halides (for example, iodides) in the presence of NaH it has been found favorable to react in a mixture of toluene and a little dimethyl formamide (0.1 to 5%, for example 0.5%).

In the alkylation it can also be provided that the compound of formula I in which $R_2$ is H or OH can first be converted to an alkali compound if it is treated with an alkali metal, alkali hydride or alkali amide (especially sodium or sodium compounds such as sodium hydride and sodamide) in an inert solvent such as dioxane, dimethyl formamide, benzene or toluene at temperatures between 0° and 150°C. and then the alkylating agent added.

Compounds of formula I wherein $N_o$ is a nitrogen atom can be converted into the corresponding N-oxide. For this purpose compounds in which $N_o$ is a nitrogen atom are reacted with hydrogen peroxide, peracetic acid or other customary peracids in inert solvents such as dilute acetic acid, ethyl acetate or acetone. The temperature employed is preferably between 0° and 50°C.

Conversely in compounds of formula I wherein $N_o$ is the group ≡ NO the oxygen atom can be removed by catalytic hydrogenation or by chemical deoxygenation. As catalysts for the catalytic hydrogenation there are suitable, for example, the customary metallic hydrogenation catalysts, especially noble metal catalysts (palladium/activated carbon, platinum) or Raney-nickel; as solvents there are preferably employed lower alcohols, e.g., methanol, ethanol and isopropanol. The temperatures employed are between 0° and 200°C., preferably between 0° and 100°C. In a given case the process can be carried out at pressures up to 50 atmospheres absolute. For chemical deoxygenation there are preferably used phosphorus trichloride or dimethyl sulfoxide in inert solvents such as dioxane, benzene or toluene at temperatures between 0° and 150°C., preferably 0° to 100°C.

Basic compounds of Formula I can be converted into their salts by conventional methods. As anions for these salts there can be employed the known and therapeutically usable (pharmacologically acceptable) acid residues. For example, there can be used acids such a sulfuric acid, phosphoric acid, hydrohalic acids, e.g., hydrochloric acid or hydrobromic acid, ethylenediamine tetraacetic acid, sulfamic acid, benzene sulfonic acid, p-toluene sulfonic acid, camphor sulfonic acid, methane sulfonic acid, guarazulene sulfonic acid, maleic acid, fumaric acid, oxalic acid, tartaric acid, lactic acid, citric acid, ascorbic acid, glycolic acid, salicyclic acid, acetic acid, propionic acid, gluconic acid, benzoic acid, acetamidoacetic acid, hydroxyethane sulfonic acid, malonic acid.

If the compounds of formula I contain acid groups they can be converted in customary manner into their alkali (e.g., sodium or potassium), ammonium or substituted ammonium salts. As substituted ammonium salts there can be used especially salts of tertiary alkyl amines, lower aminoalcohols and bis and tris(hydroxyalkyl) amines. The alkyl group contains 1 to 6 carbon atoms. Examples of such materials are trimethylamine, tributylamine, triethylamine, tripropyl amine, aminoethanol, aminopropanol, diethanooamine, dibutanol amine, triethanolamine and tripropanolamine.

The free bases of the compounds can be prepared from their salts in customary fashion, for example, by treating a solution in an organic agent such as alcohols, e.g., methanol, with soda or soda lye.

Those compounds of formula I which contain asymmetric carbon atoms and as a rule result as racemates, can be split into the optically active isomers in known manner with the help of an optically active acid. However, it is also possible to employ from the beginning an optically active starting material whereby a correspondingly optically active or diastereomer form is obtained as the end product.

The compounds of the invention are suitable for the production of pharmaceutical compositions. The pharmaceutical compositions or medicaments can contain one or more of the compounds of the invention or mixtures of the same with other pharmaceutically active materials. For the production of pharmaceutical preparations there can be used the customary pharmaceutical carriers and assistants. The medicines can be employed enterally, parenterally, orally or perlingually. For example, dispensing can take place in the form of tablets, capsules, pills, dragees, plugs, salves, jellies, creams, powders, liquids, dusts or aerosols. As liquids there can be used, for example, oily or aqueous solutions or suspensions, emulsions, injectable aqueous and oily solutions or suspensions.

For example there can be made and used in the invention compounds of formula I wherein the symbols $n$, A, $N_o$ and $R_1$ to $R_4$ have the following meanings:

$n$ is 1 to 3
A is oxygen;
$N_o$ is nitrogen;
$R_1$ is methoxy, ethoxy, propoxy, phenyl, fluorophenyl or chlorophenyl;
$R_2$ is hydrogen or hydroxy;
$R_3$ is hydrogen, fluorine, or chlorine, preferably in the ortho position;
$R_4$ is hydrogen.

The starting compounds used in process (a) can be prepared for example according to the process of German published Application No. 2,259,471 or von Bebenburg et al U.S. Pat. application Ser. No. 313,542, filed Dec. 8, 1972 or in analogous manner to those processes. The entire disclosure of the von Bebenburg et al U.S. Pat. application is hereby incorporated by reference. These starting compounds are claimed as new compounds in said von Bebenburg et al application.

The starting compounds used in process (b) for example can be made from compounds of formula IV which contain a hydrogen atom in place of the group $-(CH_2)_n - C(=A) - R_1$ (see German published application 2,259,471 and the von Bebenburg U.S. Pat. application Ser. No. 313,542) by alkylation with a compound of the formula $Hal(CH_2)_n-C(=A)R_1$, wherein Hal is a chlorine or bromine using the conditions given in those two applications.

Unless otherwise indicated, all percentages are by weight.

EXAMPLE 1

1-carbethoxymethyl-5-phenyl-7-chloro-3H-pyrido[3,2-e]-1,4-diazepinone-(2):

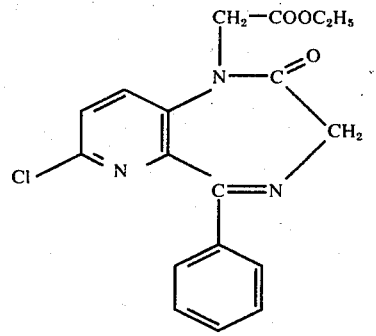

To a solution of 27 grams (0.1 mole) of 5-phenyl-7-chloro-3H-pyrido[3,2-e]-1,4-diazepinone-(2) (prepared as described in Example 1 of von Bebenburg application 313,542) in 250 ml of dimethyl formamide there were added 3.5 grams of sodium hydride (80% in white oil) at 20°C. and then the mixture stirred for 30 minutes. Then there were dropped in 13 ml of ethyl bromoacetate whereupon an exothermic reaction occurred and the temperature increased to 40°C. The mixture was stirred for another 30 minutes at 40° to 50°C, then there were dropped in 50 ml of ethanol and 20 ml of glacial acetic acid and the mixture poured into 1 liter of water. The substance crystallizing out was filtered off with suction and recrystallized from methyl ethyl ketone.

Yield 20 grams; M.P. 184° to 186°C.

EXAMPLE 2

1-β-carboxyethyl-5-phenyl-7-chloro-3H-pyrido[3,2-e]-1,4-diazepinone-(2):

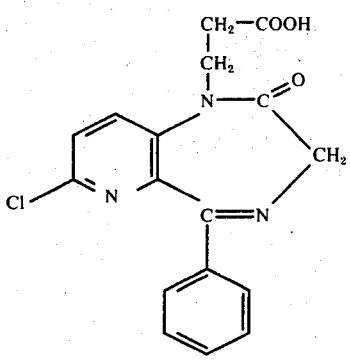

To a solution of 27 grams of 5-phenyl-7-chloro-3H-pyrido[3,2-e]-1,4-diazepinone-(2) in 200 ml of dimethyl formamide there were added with stirring in a nitrogen atmosphere 3 grams of sodium hydride (80% in white oil), the mixture stirred for 30 minutes at room temperature and then 10 ml of β-propiophenone added. The temperature increased in 30 minutes to 40°C. The mixture was stirred further for one hour, the dimethyl formamide distilled off in a vacuum and then the residue dissolved in water. The solution was decolorized with activated carbon, then acidified with glacial acetic acid. The oily product which precipitated crystallized in rubbing. It was recrystallized from chloroform/gasoline. M.P. 198°–202°C.; Yield 14 grams.

EXAMPLE 3

1-[3-cyanopropyl-(1)]-5-phenyl-7-chloro-3H-pyrido[3,2-e]-1,4-diazepinone-(2);

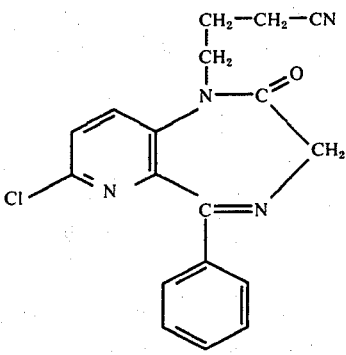

Into a mixture of 27 grams of 5-phenyl-7-chloro-3H-pyrido[3,2-e]-1,4-diazepinone-(2), 200 ml dioxane and 5 ml of dimethyl formamide there were introduced with stirring in a nitrogen atmosphere 4.5 grams of sodium hydride (57% in white oil). The temperature was increased to 30°C. then the mixture was heated to 90°C. and there were dropped in 15 grams of gamma-bromobutyronitrile. The mixture was stirred for 5 hours at 90°–95°C., then the inorganic salt was filtered off with suction and the filtrate evaporated in a vacuum. The syrupy residue was dissolved in 400 ml of chloroform, was washed 3 times with 5% aqueous sodium hydroxide and twice with water, the chloroform layer dried and treated with gasoline up to turbidity. The product in pure form crystallized out overnight. M.P. 170°–174°C.; Yield 20 grams.

EXAMPLE 4

1-benzoylmethyl-5-(o-chlorophenyl-)-7-chloro-3H-pyrido[3,2-e]-1,4-diazepinone-(2)-4-oxide:

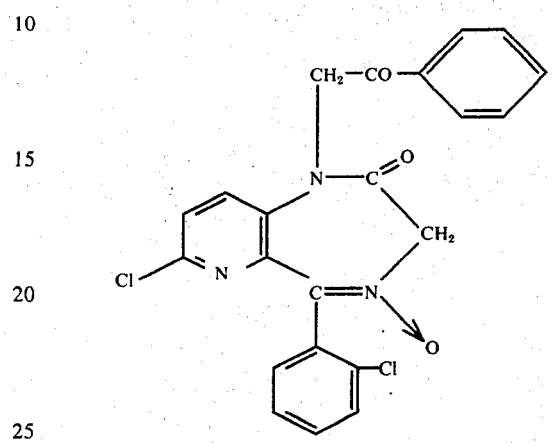

To a mixture of 16.1 grams (0.05 mole) of 5-(o-chlorophenyl)-7-chloro-3H-pyrido[3,2-e]-1,4diazepinone-4-oxide (made in a manner analogous to that used in von Bebenburg application 313,542 Example 3 for preparing 5-phenyl-7-chloro-3H-pyrido[3,2-e]1,4-benzodiazepinone-(2)-4-oxide but starting from 2-o-chlorobenzoyl-3-amino-6-chloropyridine), 200 ml of dioxane and 20 ml of dimethyl formamide there were added with stirring under a nitrogen atmosphere at room temperature 1.7 grams of sodium hydride (80% in white oil). Then there were added 8.6 grams of phenacetyl chloride and the mixture stirred 4 hours at 50°C. The product was separated by vacuum filtration from the precipitated salts, the filtrate acidified with glacial acetic acid and concentrated to one-third its volume in a vacuum. The residue crystallized. It was recrystallized from dimethyl formamide/ethanol. M.P. 240°C.; Yield 15 grams.

EXAMPLE 5

1-benzoylmethyl-5-(o-chlorophenyl-)-7-chloro-3H-pyrido-[3,2-e]-1,4-diazepinone-(2):

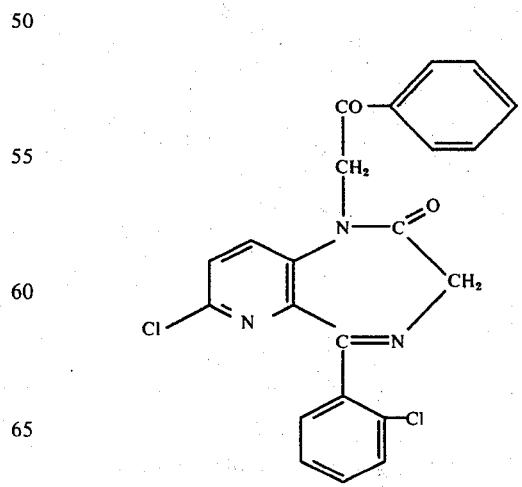

The title substance was prepared from 15.3 grams (0.05 mole) of 5-(o-chlorophenyl)-7-chloro-3H-pyrido[3,2-e]-1,4-diazepinone-(2) (prepared as set forth in Example 6 of von Bebenburg application 313,542) in a manner analogous to Example 4.

M.P. 161°–163°C.; Yield 13.5 grams.

EXAMPLE 6

1-acetylmethyl-5-phenyl-7-chloro-3H-pyrido[3,2-e]-1,4-diazepinone-(2):

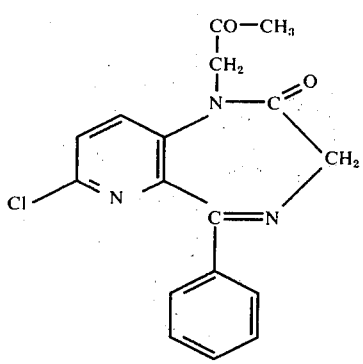

To a mixture of 27 grams (0.1 mole) of 5-phenyl-7-chloro-3H-pyrido[3,2-e]-1,4-diazepinone-(2), 400 ml of dioxane and 40 ml of dimethyl formamide there were added under nitrogen with stirring at room temperature 3.3 grams of sodium hydride (80% in white oil). After 30 minutes there were added 15.1 grams of bromoacetone and the mixture warmed with stirring for 6 hours at 40°C., wherein at intervals of 2 hours there were added each time a further 3 grams of bromoacetone. The mixture was evaporated in a vacuum, the residue dissolved in ether, the ether solution shaken several times with 5% aqueous sodium hydroxide, dried and concentrated to 100 ml. The reaction product slowly crystallized out. It was recrystallized from ethanol. M.P. 176°C., Yield 2 grams.

EXAMPLE 7

1-(2-p-chlorophenyl-2-oxo-ethyl)-5-phenyl-7-chloro-3H-pyrido[3,2-e]- 1,4-diazepinone-(2):

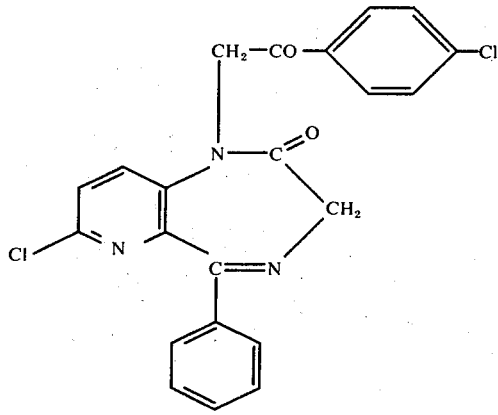

To a mixture of 27.2 grams (0.1 mole) of 5-phenyl-7-chloro-3H-pyrido[3,2-e]-1,4-diazepinone-(2), 200 ml of dioxane and 25 ml of dimethyl formamide there were added with stirring under nitrogen at 20°C. 5 grams of sodium hydride (57% in white oil). After 30 minutes there were added 25 grams of α,p-dichloroacetophenone and the mixture stirred for 2 hours at 50°C. The dimethyl formamide was evaporated off in a vacuum, the residue stirred up with water. The crystals that formed were filtered off with suction and recrystallized from dimethyl formamide/methanol.

Yield 30 grams; M.P. 216°–218°C.

EXAMPLE 8

1-cyanomethyl-5-phenyl-7-chloro-3H-pyrido[3,2-e]-1,4-diazepinone-(2):

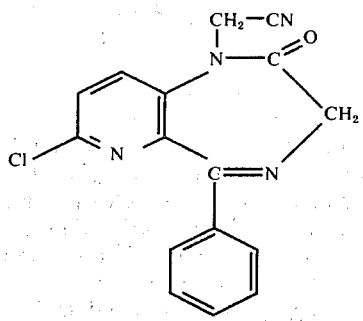

13.5 grams (0.05 mole) of 5-phenyl-7-chloro-3H-pyrido[3,2-e]1,4-diazepinone-(2) and 6 grams of chloroacetonitrile were reacted in a manner analogous to Example 7. The reaction product was recrystallized twice from acetone. Yield 6 grams; M.P. 222°–224°C.

EXAMPLE 9

1-carbethoxymethyl-5-phenyl-7-chloro3H-pyrido[3,2-e]-diazepinone-(2):

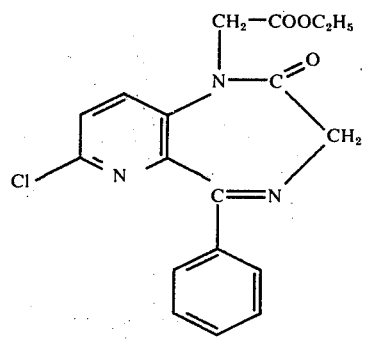

This compound was made according to process (b) as follows:

70 grams of 2-benzoyl-3[N-(carbobenzoxyaminoacetyl)-N-carbethoxymethyl]-amino-6-chloropyridine were introduced into 140 ml of a 40% solution of hydrogen bromide in glacial acetic acid, whereby the material dissolved with a strong development of gas. Then it was stirred for an addtional hour and treated with 1 liter of ether. A thick oil precipitated and the upper layer decanted off. The oil was dissolved in 100 ml of methanol and made alkaline with aqueous ammonia, whereupon after a short time the desired product crystallized out. Yield: 14 grams; M.P. 184°–186°C.

The starting material in Example 9 was produced as follows.

There were dropped into a solution of 130 grams of 2-benzoyl-3-amino-6-chloropyridine in 250 ml of chloroform at room temperature 120 ml of trifluoroacetic anhydride. After the dying away of the exothermic reaction stirring was continued for 30 minutes and then 500 ml of gasoline (60° to 80°C.) added whereupon the 2-benzoyl-3-trifluoroacetylamino-6-chloropyridine crystallized out. This was filtered off with suction and washed with ethanol. Yield 124 grams; M.P. 134° to 136°C.

66 grams (0.2 mole) of 2-benzoyl-3-trifluoroacetylamino-6-pyridine were dissolved in 500 ml of dimethyl formamide, then 10 grams of sodium hydride (57% in white oil) added at room temperature and the mixture stirred for 30 minutes. Then there were dropped in 40 ml of ethyl bromoacetate and the mixture heated at 80° to 90°C. with stirring for 5 hours. Thereupon there were dropped in 50 ml of ethanol, the solvent distilled off in a vacuum, the residue stirred with 400 ml of ethanol, a solution of 30 grams of potassium hydroxide in 150 ml of water added and the mixture warmed for 30 minutes on the water bath with stirring. Upon cooling off the potassium salt of the acid began to crystallize out. The mixture was stirred with 3 liters of water and acidified with glacial acetic acid. The precipitating crystals of the acid were filtered off with suction and washed with water. Yield of acid: 46 grams. The acid was esterified without further purification. For this purpose the 46 grams of acid were dissolved in 500 ml of ethanol and there was introduced with stirring at 60°C. hydrogen chloride until saturation occurred. Next the solution was concentrated to 200 ml and cooled while stirring. The precipitated crystals of the 2-benzoyl-3-carbethoxymethylamino-6-chloropyridine were filtered off with suction and washed with ethanol. Yield 35 grams; M.P. 88° to 90°C.

Then 37 grams of carbobenzoxy-glycine were suspended in 600 ml of diethyl ether and there were added with stirring at room temperature 40 grams of phosphorus pentachloride. The mixture was stirred for 30 minutes, whereupon everything went into solution. To this there were dropped in a solution of 35 grams of 2-benzoyl-3-carbethoxymethylamino-6-chloropyridine in 100 ml of chloroform and the mixture boiled at reflux with stirring for 12 hours. The mixture was allowed to stand at room temperature for one day and night. Then the solution was shaken with ice water and thereafter with 5% aqueous sodium hydroxide solution and then again several times with water. The organic phase was dried and evaporated in a vacuum. The oil remaining behind, which mainly consisted of the 2-benzoyl-3-[N-(carbobenzoxyamino-acetyl)-N-carbethoxymethyl]-amino-6-chloropyridne (still containing 20% unreacted 2-benzoyl-3-carbethoxymethyl-amino-6-chloropyridine) was added directly to the further reaction as set forth above to produce the compound of Example 9.

The compounds of the invention are suited for the production of pharmaceutical compositions and preparations. The pharmaceutical compositions or drugs contain as the active material one or several of the compounds of the invention, in a given case in admixture with other pharmacologically or pharmaceutically effective materials. The production of the medicine can take place with the use of known and customary pharmaceutical assistants, carriers and diluents.

Such carriers and assistants as set forth for example are those recommended in the following literature as adjuvants for pharmacy, cosmetic and related fields such as in Ullmann's Encyklopadie der technischer Chemie, Vol. 4 (1953), pages 1 to 39; Journal of Pharmaceutical Sciences, Vol. 52 (1963), pages 918 et seq.; H. v. Czetsch-Lindenwald, Hilfstoffe fur Pharmazie und angrenzende Gebiete; Pharm. Ind. Vol. 2 (1961), pages 72 et seq.; Dr. H. P. Fiedler, Lexicon der Hilfstoffe fur Pharmazie, Kosmetik und angrenzende Gebiete, Cantor Kg. Aulendorf i. Wurtt, 1971.

Examples of such materials include gelatin, natural sugars such as sucrose or lactose, lecithin, pectin, starch (for example corn starch), tylose, talc, lycopodium, silica (for example colloidal silica), glucose, cellulose, cellulose derivatives for example cellulose ethers in which the cellulose hydroxyl groups are partially etherified with lower aliphatic alcohols and/or lower saturated oxyalcohols, (for example, methyl hydroxypropyl cellulose, methyl cellulose, hydroxyethyl cellulose) stearates, e.g., methylstearate, and glyceryl stearate, magnesium and calcium salts of fatty acids with 12 to 22 carbon atoms, especially saturated acids (for example calcium stearate, calcium laurate, magnesium oleates, calcium palmitate, calcium behenate and magnesium stearate), emulsifiers, oils and fats, especially of plant origin (for example, peanut oil, castor oil, olive oil, sesame oil, cottonseed oil, corn oil, mono-, di- and triglycerides of saturated fatty acids ($C_{12}H_{24}O_2$ to $C_{18}H_{36}O_2$ and their mixtures, e.g., glyceryl monosteareate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol dipropylene glycol, polyethylene glycol 400 and other polyethylene glycols, as well as derivatives of such alcohols and polyglycols, esters of saturated and unsaturated fatty acids (2 to 22 carbon atoms, especially 10 to 18 carbon atoms), with mono- (1 to 20 carbon atoms alkanols) or polyhydric alcohols such as glycols, glycerine, diethylene glycol, pentaerythritol, sorbitol, mannitol, ethyl alcohol, butyl alchol, octadecyl alcohol, etc., e.g., glyceryl stearate, glyceryl palmitate, glycol distearate, glycol dilaurate, glycol diacetate, monoacetin, triacetin, glyceryl oleate, ethylene glycol stearate; such esters of polyvalent alcohols can in a given case also be etherified, benzyl benzoate, dioxolane, glycerine formal, glycol furfural, diemthyl acetamide, lactamide, lactates, e.g., ethyl lactate, ethyl carbonate, silicones (especially middle viscosity dimethyl polysiloxane) and the like.

For the production of solutions there can be used water or physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl acetate, partial esters of glycerine, e.g., monoacetic diacetin, glyceryl monostearate, glyceryl distearate, glyceryl monopalmitate, paraffins and the like.

In the production of the preparations there can be used known and conventional solvent aids. As solvent aids there can be used, for example, polyoxyethylated fats, e.g., polyoxyethylated oleo triglyceride, linolized oleotriglyceride. Examples of oleotriglycerides are olive oil, peanut oil, castor oil, sesame oil, cottonseed oil, corn oil (see also Dr. H. P. Fiedler, "Lexikon der Hilfsstoffe fur Pharmazie, Kosmetik und angrenzende Gebiete", 1971, pages 191 to 195.

Polyoxyethylated means that the materials in question contain polyoxyethylene chains whose degree of polymerization is generally between 2 and 40 and especially between 10 and 20. Such materials can be obtained for example by reaction of the corresponding glyceride with ethylene oxide (for example 40 moles of ethylene oxide per mole of glyceride).

Furthermore, there can be added preservatives, stabilizers, buffers, taste correctives, antioxidants and complex formers (for example ethylenediamine tetraacetic acid) and the like. In a given case for stabilization of the active molecule the pH is adjusted to about 3 to 7 with physiologically compatible acids or buffers. Generally, there is preferred as neutral as possible to weak acid (to pH 5) pH value. As antioxidants there can be used for example sodium meta bisulfite, ascorbic acid, gallic acid, alkyl gallates, e.g., methyl gallate and ethyl gallate, butyl hydroxyanisole, nordihydrogauraretic acid, tocopherols such as tocopherol and synergists (materials which bind heavy metals by complex formation, for example, lecithin, ascorbic acid, phosphoric acid). The addition of synergists increases considerably the antioxidant activity of tocopherol. As preservatives there can be used for example sorbic acid, p-hydroxybenzoic acid esters (for example lower alkyl esters such as the methyl ester and the ethyl ester benzoic acid), sodium benzoate, trichloroisobutyl alcohol, phenol cresol, benzethonium chloride and formalin derivatives.

The pharmacological and galenical treatment of the compounds of the invention takes place according to the usual standard methods. For example, the active material of materials and assistants or carriers are well mixed by stirring or homogenization (for example by means of a colloid mill or ball mill), wherein the operation is generally carried out at temperatures between 20° and 80°C., preferably 20° to 50°C.

The drugs can be used for example orally, parenterally, rectally, vaginally, perlingually, or locally.

Other medicines can also be added.

The compounds of the invention in the spasm test of Tedischi (mouse) as well as in the motility test on the mouse in the circular cage of F. Heim show a good anxiolytic (tranquilizing) and calming activity.

This activity is comparable to the activity of the known medicine Diazepoxid.

The lowest effective dosage in the above-mentioned animal experiments for example is 0.5 mg/kg body weight orally, 0.1 mg/kg sublingually and 0.05 mg/kg intravenously.

As a general dosage range there can be used, for example, 0.5 to 10 mg/kg body weight orally, 0.1 to 2 mg/kg sublingually and 0.05 to 1 mg/kg intravenously.

The compounds of the invention are useful in treating anxiety, stress and restlessness conditions, vegetative dystony, nervousness, irritability, moodiness, footlight fever (of actors), weather feelings, behavior and adaptability problems of children, functional cardiovascular, gastrointestinal and respiratory complaints. They are also useful in menstrual and climatic disturbances, aiding before operation and in assisting birth.

The pharmaceutical preparations generally contain between 1 and 10% of the active component (or components) of the invention.

The compounds can be delivered in the form of tablets, capsules, pills, dragees, suppositories, salves, gels, creams, powders, liquids, dusts or aerosols. As liquid there can be used oily or aqueous solutions or suspensions, emulsions. The preferred forms of use are as tablets which contain between 0.1 and 50 mg of active material or solutions which contain between 0.1 and 5% of active material.

In individual doses the amount of active component of the invention can be used for example in an amount of:
a. in oral dispensation between 1 and 50 mg;
b. in parenteral dispensation (for example, intravenously, intramuscularly) between 0.1 and 5 mg;
c. in inhalation dispensation (solutions or aerosols) between 0.5 and 10 mg;
d. in rectal or vaginal dispensation between 1 and 50 mg.

(The dosages in each case are based on the free base).

For example, there is recommended the use of 1 to 3 tablets containing 1 to 50 mg of active ingredient 3 times daily or for example intravenously the injection 1 to 3 times daily of a 1 to 2 ml ampoule containing 0.1 to 10 mg of active substance. In oral preparations the minimum daily dosage for example is 3 mg; the maximum daily dosage should not be over 200 mg.

In the treatment of dogs and cats the oral individual dosage in general is between 0.5 and 50 mg/kg body weight; the parenteral individual dosage is between about 0.1 and 10 mg/kg body weight. In the treatment of horses and cattle, the individual dosage orally is generally between 5 and 100 mg/kg; the parenteral individual dosage is between 1 and 20 mg/kg body weight.

The acute toxicity of the compounds of the invention in the mouse (expressed by the $LD_{50}$ mg/kg method of Miller and Tainter, Proc. Soc. Exper. Biol. and Med., Vol. 57 (1944), pages 261, et seq.) in oral application is between 500 mg/kg and 10,000 mg/kg (or above 8000 mg/kg).

The drugs can be used in human medicine, in veterinary medicine, e.g., to treat cats, dogs, horses, sheep, cattle goats and pigs or in agriculture. The drugs can be used alone or in admixture with other pharmacologically active materials.

The salts can also be used as curing agents for melamine-formaldehyde resins.

EXAMPLE 10

1-Cyanomethyl-5-(o-chlorophenyl)-7-chloro-3H-pyrido[3,2-e]-1,4-diazepinone-(2)

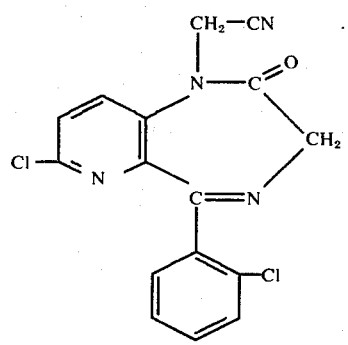

To a mixture of 15.2 grams (0.05 mole) of 5-(o-chlorophenyl)-7-chloro-3H-pyrido[3,2-e]-1,4-diazepinone-(2), 200 ml of dioxane and 25 ml of dimethyl formamide there were added with stirring and under a nitrogen atmosphere at 20°C. 2.5 grams of sodium hydride (57% in white oil). After 30 minutes there were added 6 grams of chloroacetonitrile and the mixture stirred at 50°C. for 2 hours. The dimethyl formamide was evaporated in a vacuum, the residue stirred with water and the crystals obtained removed with suction. These crystals were recrystallized from ethanol/dimethyl formamide (95:5 by volume). Yield 13 grams. M.P. 176°C.

EXAMPLE 11

1-Cyanomethyl-5-(o-chlorophenyl)-7-chloro-3H-pyrido[3,2-e]-1,4-diazepinone-(2)-4-oxide

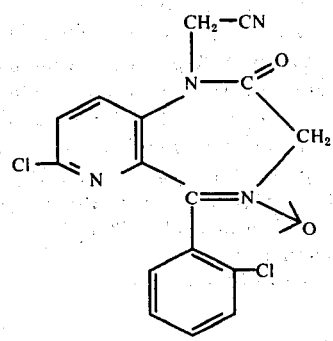

To a mixture of 32.2 grams (0.1 mole) of 5-(o-chlorophenyl)-6-7-chloro-3H-pyrido[3,2-e]-1,4-diazepinone-(2)-4-oxide, 200 ml of dioxane and 25 ml of dimethyl formamide there were added with stirring and under nitrogen at 20°C 5 grams of sodium hydride (57% in white oil). After 30 minutes there were added 12 grams of chloroacetonitrile and the mixture stirred at 50°C. for 2 hours. The dimethyl formamide was evaporated in a vacuum, the residue stirred with water and the crystals obtained removed with suction. These crystals were recrystallized from ethanol/dimethyl formamide (95:5 by volume). Yield 21.5 grams. M.P. 220°C.

EXAMPLE 12

1-Cyanomethyl-3-hydroxy-5-(o-chlorophenyl) 7-chloro-3H-pyrido[3,2-e]-1,4-diazepinone-(2)

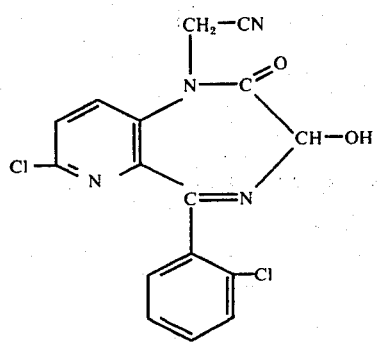

15 grams of 1cyanomethyl-5-(o-chlorophenyl)-7-chloro-3H-pyrido[3,2-e]-1,4-diazepinone-(2)-4-oxide were boiled under reflux with stirring in a mixture of 30 ml of glacial acetic acid and 30 ml of acetic anhydride for 20 minutes. The starting material thereupon went into solution under an exothermic reaction. Upon cooling the reaction solution the reaction product crystallized out. It was filtered off with suction and washed with acetic acid and water. Yield 15 grams. M.P. 248°C. The thus obtained 1-cyanomethyl-3-acetoxy-5-(o-chlorophenyl)-7-chloro-3H-pyrido[3,2-e]-1,4-diazepinone-(2) was suspended with strong stirring in 600 ml of methanol, the mixture brought to boiling and 2 ml of 6N isopropanolic HCl solution added. Then the mixture boiled for 15 minutes with stirring and reflux and there in the course of 30 minutes there were distilled off 400 ml of methanol. The solution was filtered with suction while hot from some unreacted acetoxy compound, there innoculated with seeds and cooled while stirring. The precipitated product was recrystallized once more from chloroform/ether. Yield 5 grams. M.P. 178°–180°C.

EXAMPLE 13

1-Thiocarbamoylmethyl-5-phenyl-7-chloro-3H-pyrido[3,2e]-1,4diazepinone-(2)

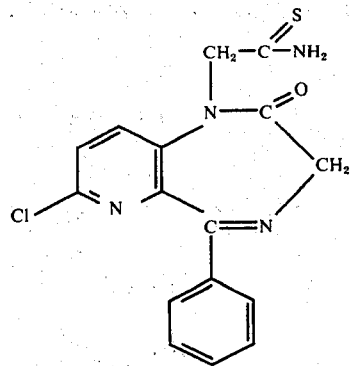

24 grams of 1-cyanomethyl-5-phenyl-7-chloro-3H-pyrido[-3,2-e]-1,4-diazepinone-(2) were dissolved in a solution of 20 grams of ammonia in 500 ml of ethanol and hydrogen sulfide was introduced into the solution at room temperature over a period of 150 minutes. The reaction is slightly exothermic, the reaction product precipitated out. It was filtered off with suction and recrystallized from dimethyl formamide-ethanol. Yield 20 grams. M.P. 216°C. (decomposition).

EXAMPLE 14

1-Acetylmethyl-5(o-chlorophenyl)-7-chloro-3H-pyrido[3,2-e]-1,4-diazepinone-(2)-oxide-(4)

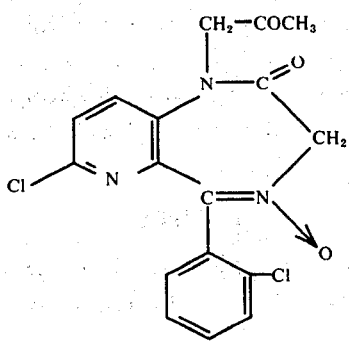

To a mixture of 32 grams of 5-(o-chlorophenyl)-7-chloro-3H-pyrido[3,2-e]-1,4-diazepinone-(2)-oxide-(4) and 250 ml of dimethyl formamide there were added with stirring under nitrogen at room temperature 3.3 grams of sodium hydride (80% in white oil). After 30 minutes there were added 13.5 grams of chloroacetone in 30 ml of dimethyl formamide. After the exothermic reaction the mixture was warmed with stirring for 1 hour at 60°C then there were again added 5 grams of chloroacetone in 20 ml of dimethyl formamide and the mixture heated a further hour at 60°C. The reaction mixture after addition of 20 ml of ethanol was poured into 1 liter of water. The precipitated reaction product was recrystallized from ethanol. Yield 15 grams. M.P. 112°–113.5°C.

EXAMPLE 15

1-Acetylmethyl-3-hydroxy-5-(o-chlorophenyl)-7-chloro-3H-pyrido[3,2-e]-1,4-diazepinone-(2)

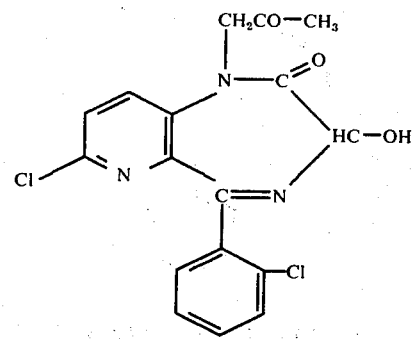

15 grams of 1-acetylmethyl-3-hydroxy-5-(o-chlorophenyl)-7-chloro-3H-pyrido[3,2-e]-diazepinone-(2)-oxide-(4) were dissolved with stirring in a mixture of 75 ml acetic acid and 75 ml of acetic anhydride and boiled at reflux for 45 minutes. Upon cooling the 3-acetoxy compound crystallized out, which compound was immediately further reacted after washing with water and a little methanol. It was dissolved in 100 ml of n-propanol and there were added at room temperature with stirring 5 grams of powdered potassium hydroxide. After stirring for 30 minutes it was acidified with acetic acid and 200 ml of water added. The precipitated product was recrystallized from ethanol. Yield 3 grams. M.P. 235°–237°C.

EXAMPLE 16

1-Thiocarbamoylmethyl-5-(o-chlorophenyl)-7-chloro-3H-pyrido[3,2-e]-1,4-diazepinone-(2)

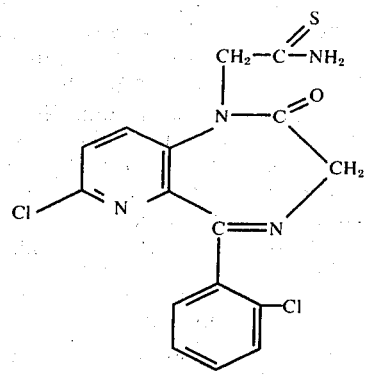

26 grams of 1-cyanomethyl-5-(o-chlorophenyl)-7-chloro-3H-pyrido[3,2-e]-1,4-diazepinone-(2) were dissolved in a solution of 20 grams of ammonia in 500 ml of ethanol and hydrogen sulfide was introduced into the solution over a period of 150 minutes at room temperature. The reaction is slightly exothermic, the reaction product precipitated out. It was filtered off with suction and recrystallized from dimethylformamide-ethanol. Yield 20 grams. M.P. 204°C.

What is claimed is:

1. A compound of the formula:

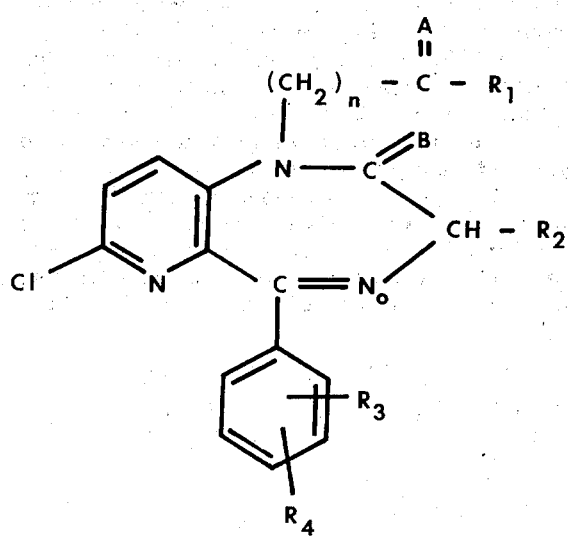

wherein:

$n$ is an integer from 1 to 4;

is (a)

where $R_1$ is alkyl of 1 to 6 carbon atoms, (b) —CN, or (c)

B is oxygen;
$R_2$ is hydrogen or hydroxyl;
$N_o$ is nitrogen or an N-oxide group;
$R_3$ is hydrogen or chlorine;
$R_4$ is hydrogen;
the tautomeric forms thereof and pharmaceutically acceptable salts thereof.

2. A compound according to claim 1 wherein

is (a).

3. A compound according to claim 2 wherein $R_1$ is methyl and $n$ is 1.

4. A compound according to claim 3 wherein $R_2$ is hydrogen.

5. A compound according to claim 4 wherein $R_3$ is chlorine.

6. A compound according to claim 5 which is 1-acetylmethyl-5-(o-chlorophenyl)-7-chloro-3H-pyrido[3,2-e]-1,4-diazepinone-(2)-oxide-(4).

7. A compound according to claim 3 wherein $R_2$ is hydroxyl.

8. A compound according to claim 7 wherein $R_3$ is chlorine.

9. A compound according to claim 8 which is 1-acetylmethyl-3-hydroxy-5-(o-chloro-phenyl)-7-chloro-3H-pyrido[3,2-e]-1,4-diazepinone-(2).

10. A compound according to claim 1 wherein

is (b).

11. A compound according to claim 10 wherein $n$ is 1.

12. A compound according to claim 11 where $R_2$ is hydrogen.

13. A compound according to claim 12 where $R_3$ is chlorine.

14. A compound according to claim 13 which is 1-cyanomethyl-5-(o-chlorophenyl)-7-chloro 3H-pyrido[3,2-e]-diazepinone-(2).

15. A compound according to claim 13 which is 1-cyanomethyl-5-(o-chlorophenyl)-7-chloro-3H-pyrido[3,2-e]-1,4-diazepinone-(2)-4-oxide.

16. A compound according to claim 11 where $R_2$ is hydroxyl.

17. A compound according to claim 16 where $R_3$ is chlorine.

18. A compound according to claim 17 which is 1-cyanomethyl-3-hydroxy-5-(o-chlorophenyl)-7-chloro-3H-pyrido[3,2-e]-1,4-diazepinone-(2).

19. A compound according to claim 1 wherein

is (c).

20. A compound according to claim 19 wherein $n$ is 1.

21. A compound according to claim 20 wherein $R_2$ is hydrogen.

22. A compound according to claim 21 wherein $R_3$ is chlorine.

23. A compound according to claim 22 which is 1-thiocarbamoylmethyl-5-(o-chlorophenyl)-7-chloro-3H-pyrido[3,2-e]-1,4-diazepinone-(2).

24. A compound according to claim 21 wherein $R_3$ is hydrogen.

25. A compound according to claim 24 which is 1-thiocarbamoylmethyl-5-phenyl-7-chloro-3H-pyrido[3,2-e]-1,4-diazepinone-(2).

* * * * *